United States Patent [19]

Vieillard

[11] Patent Number: 4,879,432

[45] Date of Patent: Nov. 7, 1989

[54] METHOD FOR MEASURING THE COAGULATION OF BLOOD PLASMA

[76] Inventor: Didier Vieillard, Polyclinique du Parc Route d'Assevent, 59600 Maubeuge, France

[21] Appl. No.: 277,510

[22] Filed: Nov. 30, 1988

Related U.S. Application Data

[63] Continuation of Ser. No. 850,623, Apr. 11, 1986, abandoned.

[30] Foreign Application Priority Data

Apr. 11, 1985 [FR] France .................. 85 05472

[51] Int. Cl.$^4$ ........................... G01N 33/86
[52] U.S. Cl. ................... 436/69; 436/164; 73/64.1; 73/54; 73/57; 422/73
[58] Field of Search .......... 73/64.1, 54, 57; 422/73; 436/69, 164

[56] References Cited

U.S. PATENT DOCUMENTS

| | | | |
|---|---|---|---|
| 2,731,828 | 1/1956 | Parrette et al. | 73/57 |
| 3,635,680 | 1/1972 | Peoples et al. | 422/73 |
| 3,854,324 | 12/1974 | Altshuler et al. | 73/64.1 |
| 4,000,972 | 1/1977 | Braun et al. | 436/69 |
| 4,074,971 | 2/1978 | Braun et al. | 436/69 |
| 4,497,774 | 2/1985 | Scordato | 422/73 |
| 4,533,519 | 8/1985 | Baugh et al. | 436/69 |
| 4,534,959 | 8/1985 | Smith et al. | 422/73 |

FOREIGN PATENT DOCUMENTS 2163483 7/1973 France .

*Primary Examiner*—Barry S. Richman
*Assistant Examiner*—Lyle Alfandary Alexander
*Attorney, Agent, or Firm*—Fleit, Jacobson, Cohn, Price, Holman & Stern

[57] ABSTRACT

The invention provides a method and apparatus for measuring the coagulation of blood. The principle thereof is to detect, at the beginning of coagulation, the stopping of a stream of corpuscles established in a measurement tube (1), the detection being accomplished by means of photoelectric cells or similar (15, 16). A processor (17) allows the measurement of the coagulation rate to be made automatically and displayed. The corpuscles may be microscopic gas bubbles (12) or gains of a powder having a high degree of wettability.

5 Claims, 1 Drawing Sheet

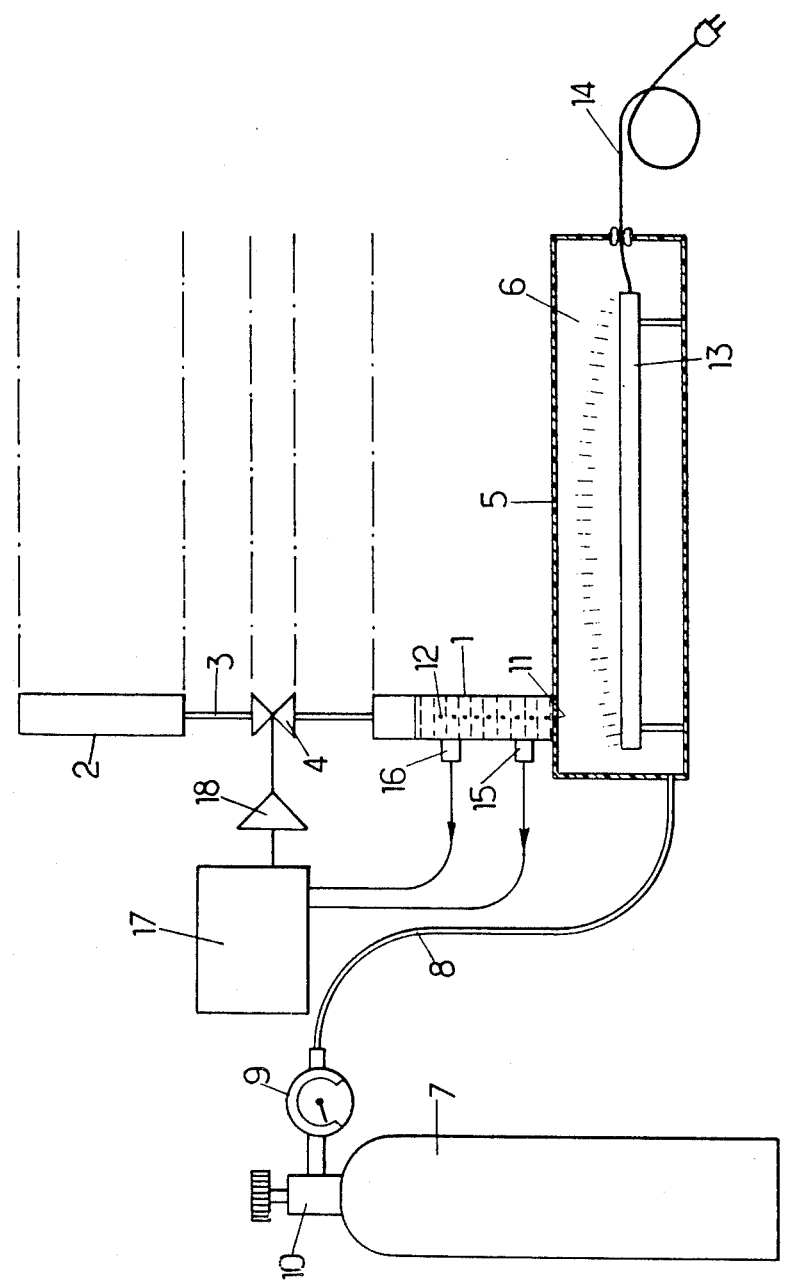

METHOD FOR MEASURING THE COAGULATION OF BLOOD PLASMA

This application is a continuation of application Ser. No. 850,623, filed Apr. 11, 1986, now abandoned.

The present invention relates to a method and apparatus for measuring the coagulation of blood plasma.

As is known, coagulation is the physical change of state of plasma, which is initially liquid and which is transformed into a gel during polymerization of the fibrinogen.

Presently known methods or apparatus, used for detecting this change of state, are essentially of two types: photometric or mechanical.

In the photometric methods, the opacity of the plasma is measured, for example by means of a light source and a cell, for the opacity increases at the time of coagulation. However, there is no exact coincidence between the two phenomena, and the measurement can therefore not be very accurate.

In the so called mechanical methods, the variations of the mechanical properties of the plasma are measured which accompany coagulation.

In some apparatus, a magnetic bar subjected to the field of a mobile external magnet is placed at the bottom of the measuring tube containing the plasma. Stopping of the rotation or of the oscillations of the bar are detected which occur at the time of coagulation.

In other apparatus, on the contrary, an external magnet keeps a ball immobile at the bottom of a rotating tube, and driving of the ball is detected which occurs at the time of coagulation.

These mechanical means, in which the increase in the mechanical resistance of a clot during coagulation is used, are not sufficiently accurate either, for the coagulation must be relatively advanced for an appreciable increase of this mechanical resistance to be observed.

It should further be noted that these methods cannot be validly used in the case of a dilute plasma for the mechanical type phenomena mentioned above are even less clear cut.

The aim of the present invention is to overcome these different drawbacks of known methods and in particular to increase the accuracy of the measurement. It is also fitting to put into practice a measurement principle which may be readily automated.

For this, a method for measuring the coagulation of blood plasma is, in accordance with the invention, essentially characterized in that in a tube a stream of gaseous or solid particles is established and the space of time is measured between a given reference time and the moment at which the stream of particles is stopped because of the coagulation, said space of time being representative of the coagulation rate.

Of course, a significant time will be taken as time reference, which as a general rule will be the time when the appropriate reagent is introduced into the tube.

This new measuring principle has proved capable of providing extremely accurate and faithful measurements, because the stopping of the stream of particles may be observed exactly at the time when the coagulation process begins. This stream may be a stream going down in the tube under the effect of gravity. In this case the particles are grains of a powder having a high degree of wettability, introduced in the upper part of the tube, the dimensions of these grains, for example glass, being extremely reduced, of the order of a few microns, so that they are immediately stopped by the fibrin network as soon as coagulation begins, even in diluted blood.

In a variant of the method, putting essentially the same principle into practice, said particles may be gas bubbles and for this a flow of compressed gas is established in the bottom of the tube and the gas flows through the tube so as to create a series of bubbles of very small diameter rising through said plasma.

Hereagain, this measuring principle has proven capable of providing extremely accurate and faithful measurements, for stopping of the rising movement of the bubbles may again be observed exactly at the time when the coagulation process begins. It is in fact possible to create at the bottom of the plasma sufficiently fine gas bubbles, for example of a diameter of the order of 30 to 60 micron, so that they are stopped instantaneously by the fibrin network, as soon as it forms, which marks precisely the beginning of coagulation.

Stopping of the particles (grains of powder or bubbles) may be detected visually by the operator, who may measure the space of time in question with a chronometer and note the result each time.

However, it will be advantageous to carry out the process automatically, especially in the case of a large number of tests, using an apparatus for implementing the above defined method.

The invention relates then further to an apparatus for measuring the coagulation of blood plasma, essentially characterized in that it comprises: at least one measuring tube associated with means adapted for automatically introducing the plasma and the reagent therein at a given time serving as time reference; means for introducing said particles into the tube so as to create therein a stream of said particles; means for detecting the stopping of said stream, and means for measuring the time elapsing between said reference time and said stopping.

In the case where the particles are gas bubbles, such an apparatus will comprise means for introducing a compressed gas through an ultrafine passageway into the bottom of said tube and means for detecting the stopping of the rising movement of the series of bubbles thus created in the tube.

One embodiment of such an apparatus will now be described by way of example which is in no way limiting with reference to the single FIGURE of the accompanying drawings which is a schematical representation thereof.

In this FIGURE for the sake of simplicity only one measuring tube has been shown out of a series of tubes which may comprise any number thereof. Similarly, only the means associated with this tube have been shown for automatically introducing plasma and reagents, these means being the same for all the tubes 1 of the series and being moreover controlled individually, by groups, or else all simultaneously. These means may comprise for example a feed tube 2 communicating with the corresponding measuring tube 1 through a duct 3 having a valve which may be controlled automatically, an electromagnetic valve 4. Tube 2 may receive successively the plasma and the reagent, but two separate tubes 2 may be used for successively feeding the plasma and the reagent into the measuring tube 1.

The series of tubes 1 which are thermostatically controlled at 37° C. rest on the upper wall 5 of an enclosure 6 connected to a compressed air cylinder 7 through a duct 8. A pressure gauge 9 placed at the outlet of the pressure reducer 10 of the cylinder allows the pressure of the air injected into closure 6 to be controlled. This pressure may be of the order of 200 cm of water column.

Enclosure 6 communicates with the bottom of each tube 1 through an ultrafine bore 11 pierced through wall 5 so that a series of microscopic bubbles 12 rise through the plasma-reagent mixture introduced into tube 1.

The choice of the diameter of holes 11 is very important for if this diameter is too great the bubbles will be too large and will not be immediately stopped as soon as the fibrin network appears. On the other hand, if this diameter is too small, stopping of the bubbles will be more difficult to detect, the holes will be extremely difficult to form and risk of clogging thereof will be too high.

A hole diameter 11 reconciling all these different requirements will be about 50 $\mu$.

So that bubbles 12 are easy to detect, either with the naked eye or using an appropriate apparatus, enclosure 6 contains a lighting lamp 13 which may be connected to the mains by a flex 14 and illuminating the bubbles 12 through the holes 11.

For detecting the bubbles, one or more photoelectric cells may be used in the automatic apparatus at present described and for each tube 1. In the FIGURE, two cells 15 and 16 have been shown spaced apart on tube 1, which, using the difference of the passage times $\delta t$ allows the speed of bubbles 12 to be checked. As soon as the speed drops to zero (stopping of the bubbles), at time $t_1$, the coagulation time $\delta t$ may be obtained by the difference with time $t_O$ when the reagent was introduced into tube 1, by controlling the opening of the electromagnetic valve 4: $\Delta t = t_1 - t_O$.

From this measurement of the coagulation time, an electronic microprocessor block 17, to which the photoelectric cells 15 and 16 are connected, can calculate the coagulation factors, for expressing the rate in % of the normal, tube by tube or simultaneously for the whole series of tubes.

The accuracy of the measurement of $\Delta t$ is excellent of the order of 1/10th of a second for a coagulation time of 10 to 40 seconds.

In the FIGURE an amplifier 18 is shown. Amplifier 18 may be fed with a signal provided by the microprocessor 17 to automatically control the opening of electromagnetic valve 4 at the reference $t_o$.

The microprocessor may of course also ensure all the other sequential controls required, storage of the measurements in a memory, digital display of the results, regulation of the different physical parameters of the different tests, etc.

The main tests which can be carried out using an apparatus of the present invention are the following:
prothrombine rate,
kaolin cephalin time,
quantity determination of the factors I, II, V, VII, VIII, IX,
Howell's time
quantity determination of antithrombine III, For Howell's time, it has been discovered that an apparatus in accordance with the invention allowed it to be measured with as good an accuracy as for manual operation, which is not the case of apparatus known up to present.

As is evident and as follows moreover already from what has gone before, the invention is in no way limited to those of its modes of application and embodiments which have been more especially considered; it embraces, on the contrary, all variants thereof.

For example, the electromagnetic valve such as 4 could of course be replaced by any other device of appropriate medical type, for example by peristaltic type valves.

In the case where a stream of particles are used which are not gas bubbles, but powder grains, the apparatus may be substantially similar to the one which has just been described, but with means, particularly for supplying the tubes with powder, for example microscopic glass balls, and possibly in so far as the detection means are concerned. In any case, an enclosure will not have to be provided with compressed air and the need of forming microscopic holes in the bottom of the tube is obviated, which may be advantageous from the economic point of view.

When powder grains are used, the powders should preferably have a density close to that of water, have a high degree of wettability and be refractive, such as glass, so that the onset of coagulation—even that of very dilute blood—may be detected. With use of the powder, other types of analyses may additionally be performed requiring very fine measurement means.

I claim:

1. A method for measuring the coagulation time of blood plasma comprising the steps of:
   (a) introducing the plasma and at least one reagent initiating coagulation of said plasma in a substantially vertical tube having an upper part while noting a reference time,
   (b) introducing through the upper part of said tube into said plasma, solid particles having a high degree of wettability and having dimensions of about a few microns, for forming a continuous stream of said particles moving downwardly into said plasma,
   (c) automatically detecting the occurrence of the instantaneous stop of downward motion of said particles in said plasma through optoelectronic means, said occurrence of said stop of downward motion indicating coagulation of said plasma, while noting the time of occurrence of said stop, and
   (d) measuring the time difference between the reference time and the time of occurrence of said stop of downward motion of particles.

2. A method for measuring the coagulation rate of blood plasma comprising the steps of:
   (a) introducing the plasma into a measuring tube,
   (b) continuously delivering gaseous or solid particles in said plasma to form a continuous vertical train of said particles moving vertically within said blood plasma,
   (c) introducing at least one reagent into said plasma for initiating coagulation of said plasma while noting the time of introduction,
   (d) automatically detecting the occurrence of the instantaneous stop of vertical motion of said particles in said plasma through optoelectronic means, said occurrence of said stop of vertical motion indicating coagulation of said plasma, while noting the time of occurrence of said stop of vertical motion,
   (e) measuring the difference between said time of introduction and said time of occurrence of said stop of vertical motion, and
   (f) automatically comparing said time difference with a normal coagulation time of a reference blood plasma for deriving an indication as to the coagulation rate of said plasma therefrom.

3. The method according to claim 2, wherein said particles are solid grains of a powder with a high degree of wettability and said particles are introduced into an upper part of said measuring tube.

4. The method according to claim 2, wherein said measuring tube has a bottom formed with a single hole and said particles are gas bubbles which are introduced into said measuring tube through said single hole.

5. The method according to claim 4, wherein the diameter of said gas bubbles are from about 30 to 60 microns.

* * * * *